(12) United States Patent
Park et al.

(10) Patent No.: US 8,846,322 B2
(45) Date of Patent: Sep. 30, 2014

(54) METHOD AND KIT FOR ISOLATING TARGET CELL

(75) Inventors: Jong-myeon Park, Incheon (KR); Jeong-gun Lee, Seoul (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 0 days.

(21) Appl. No.: 13/582,931

(22) PCT Filed: Mar. 7, 2011

(86) PCT No.: PCT/KR2011/001561
§ 371 (c)(1),
(2), (4) Date: Nov. 13, 2012

(87) PCT Pub. No.: WO2011/108909
PCT Pub. Date: Sep. 9, 2011

(65) Prior Publication Data
US 2013/0052664 A1 Feb. 28, 2013

(30) Foreign Application Priority Data

Mar. 5, 2010 (KR) .................. 10-2010-0020079
Mar. 3, 2011 (KR) .................. 10-2011-0019095

(51) Int. Cl.
*G01N 33/53* (2006.01)
*G01N 33/574* (2006.01)
*G01N 33/543* (2006.01)
*G01N 33/569* (2006.01)

(52) U.S. Cl.
CPC ........ *G01N 33/57484* (2013.01); *G01N 33/574* (2013.01); *G01N 33/543* (2013.01); *G01N 33/54313* (2013.01); *G01N 33/54353* (2013.01); *G01N 33/56966* (2013.01)
USPC .......... 435/7.1; 435/7.21; 435/7.23; 435/7.24

(58) Field of Classification Search
CPC .................................................... G01N 33/53
See application file for complete search history.

(56) References Cited

U.S. PATENT DOCUMENTS

2002/0009759 A1   1/2002   Terstappen et al.
2006/0228737 A1*  10/2006  Hwang et al. ............... 435/6

FOREIGN PATENT DOCUMENTS

KR   1020087032034 A    3/2009
WO   WO 99/29703 A2     6/1999
WO   WO 2005/106047 A2  11/2005
WO   WO 2008/005479 A2  1/2008

OTHER PUBLICATIONS

Young-Eun Choi et al., Nanotechnology for Early Cancer Detection, Sensors, 2010, 428-455, 10, doi:10.3390/s100100428.
Charalambos Kaittanis et al., The role of nanoparticle valency in the nondestructive magneticrelaxation-mediated detection and magnetic isolation of cells in complex media, J Am Chem Soc. 2009, 12780-12791, 131-35, doi:10.1021/ja9041077.
International Search Report prepared by the International Searching Authority in application No. PCT/KR2011/001561, mailed on Dec. 7, 2011.
Davies, Derek, "Chapter 11: Cell Sorting by Flow Cytometry," *Flow Cytometry: Principles and Applications*, 257-276 (Jul. 3, 2007, Human Press Inc.).
Sigma-Aldrich Inc, "Polystyrene Latex Beads Product Information," 1-7 (Nov. 1, 2000).
European Patent Office, Extended European Search Report in European Patent Application 11750966.1(Jun. 28, 2013).

* cited by examiner

*Primary Examiner* — Peter J Reddig
(74) *Attorney, Agent, or Firm* — Leydig, Voit & Mayer, Ltd.

(57) ABSTRACT

Provided are a method and kit for isolating a target cell by using particles comprising polymers having positive charge and negative charge and at least one antibody bound to polymers. The target cell in the biological sample may be efficiently isolated and detected by using a method and kit according to an exemplary embodiment.

16 Claims, 7 Drawing Sheets

METHOD AND KIT FOR ISOLATING TARGET CELL

CROSS-REFERENCE TO RELATED APPLICATIONS

This patent application is a national phase of International Patent Application No. PCT/KR2011/001561, filed Mar. 7, 2011, which claims the benefit of Korean Patent Application No. 10-2010-0020079, filed Mar. 5, 2010, and Korean Patent Application No. 10-2011-0019095, filed Mar. 3, 2011.

TECHNICAL FIELD

The present disclosure relates to methods and kits for isolating a target cell by using particles comprising polymers having positive charge and negative charge and at least one antibody bound to polymers.

BACKGROUND ART

The majority of deaths associated with malignant tumor are due to the metastasis of the original tumor cells to tissues and organs distant from the initial tumor. Accordingly, early diagnosis of metastasis is a critical factor for the survival of a cancer patient, and early diagnosis of tumor and monitoring of tumor growth are considered as very important factors for successful treatment of a cancer patient. The diagnosis of cancer usually uses diagnosis techniques by histopathology. The histopathological diagnosis technique is a method of using a tissue sample from a living subject to diagnose a cancer. Such a histopathological approach allows a tumor cell to be directly observed. However, it may be incorrect whether there is a tumor from a tissue site selected in order to obtain a sample from a living subject, and only data about a particular site obtained from the living subject are provided and thus it is difficult to know whether tumor has metastasized to another site. For this reason, the applicability in diagnosing and monitoring tumors may be limited.

It is known that circulating tumor cells (CTCs) are found from a patient before the tumor is originally detected. Accordingly, CTCs may play an important role in early diagnosis and prognosis of cancers. In addition, because cancer usually metastasizes through blood, CTC may be a marker for determining whether cancer has metastasized. Even after cancer cells have been removed by surgery, CTCs may be still exist and cancer may reoccur. However, very small amounts of these CTCs are found in blood and the cells are themselves weak, and thus it is very difficult to detect them and grasp the number of the cells. Accordingly, there still remains a need for a diagnosis method that is highly sensitive to detect CTCs, cancer cells, or cancer stem cells in a patient's body.

CTC separation methods by using magnetic nanoparticles are described in the related art. However, the method according to the related art is disadvantageous because the processes are very complicated, for example, the method of separating serum from blood, and using the affinity of biotin and streptavidin even in a magnetic separation process have a risk of losing of CTCs in the separation steps.

Accordingly, there still remains a need for a method for efficiently separating tumor cells from a biological sample and an apparatus associated with that.

DISCLOSURE OF INVENTION

Technical Problem

Provided are particles comprising at least one polymer having negative charges and at least one antibody bound to the polymer, wherein the antibody specifically binds to a surface marker of at least one target cell.

Provided are particles comprising at least one polymer having positive charges and at least one antibody bound to the polymer, wherein the antibody specifically binds to a surface marker of at least one target cell.

Provided are methods and kits for isolating a target cell from a biological sample.

Additional aspects will be set forth in part in the description which follows and, in part, will be apparent from the description, or may be learned by practice of the presented embodiments.

Solution to Problem

According to an aspect of the present invention, particles comprising at least one polymer having negative charges and at least one antibody bound to the polymer, wherein the antibody specifically binds to a surface marker of at least one target cell, are provided.

The term "particle" used herein refers to a particle that can be changed electrostatic properties according to the pH of the ambient environment. According to an exemplary embodiment, the particle may be a charge reversible bead.

The term "polymer" used herein refers to a class of macromolecules composed of repeating monomers. The polymer may include homopolymers, heteropolymers, or copoloymers. The polymer may include linear polymers or branched polymers.

The polymer serves to change electrostatic properties of the particle according to the pH of the ambient environment. The polymer having negative charges may be selected from the group consisting of polystyrenesulfonate, polyacrylic acid, polymethacrylic acid, polyalcohol, polyphosphate, polymaleic acid, hyaluronic acid, and any combinations thereof, but it is not limited thereto. For example, when a particle comprising polymaleic acid is present in a solution having a pH value higher than a pKa value of the polymaleic acid, the particle may be negative. On the other hand, when the particle comprising polymaleic acid is present in a solution having a pH value lower than a pKa value of the polymaleic acid, the particle may be neutral.

According to an exemplary embodiment, the polymer may have a molecular weight of about 1,000 to about 100,000 or of about 3,000 to about 50,000. The polymer may be linked to the particle to increase the charge density. Also, the polymer may provide functional groups to bind at least one antibody, which at least one antibody specifically binds to a surface marker of a target cell.

According to another aspect of the present invention, particles comprising at least one polymer having positive charges and at least one antibody bound to the polymer, wherein the antibody specifically binds to a surface marker of at least one target cell, are provided.

The polymer serves to change electrostatic properties of the particle according to the pH of the ambient environment. As described above, the polymer having positive charges may be selected from the group of, for example, polyaniline, polypyrrol, polyethyleneimine, polylysine, chitosan, and any combinations thereof, but it is not limited thereto. For example, when a particle comprising polyethyleneimine is present in a solution having a pH value lower than a pKa value of the polyethyleneimine, the particle may be positive. On the other hand, when the particle comprising polyethyleneimine is present in a solution having a pH value higher than a pKa value of the polyethyleneimine, the particle may be neutral.

According to an exemplary embodiment, the polymer may have a molecular weight of about 100 to about 50,000 and of about 400 to about 25,000. The polymer may be linked to the particle to increase the charge density. Also, the polymer may provide functional groups to bind at least one antibody, which at least one antibody specifically binds to a surface marker of a target cell.

At least one antibody specifically binds to a surface marker of at least one target cell.

The term "target cell" used herein refers to a cell having a surface marker on a cell surface. The target cell may be selected from the group of, for example, circulating tumor cell, cancer stem cell, immunocyte, fetal stem cell, fetal cell, cancer cell, tumor cell, and any combinations thereof, but it is not limited thereto.

The term "surface marker" used herein refers to any substance which exists on the surface of the target cell and may differentiate the target cell from other cells in a biological sample. The surface marker may be selected from the group consisting of protein, polysaccharide, lipid, nucleic acid, and any combinations thereof, but it is not limited thereto. According to an exemplary embodiment, the surface marker may be a protein which is specifically expressed in a target cell and displayed on a cell membrane. For example, the protein may be selected from the group consisting of estrogen receptor, progesterone receptor, synaptophysin, mucin 1 (MUC 1), Bcl-2, MIB1/Ki67, cyclin D1, cyclin E, p27, topoisomerase IIa, cyclooxygenase 2, ERK1/ERK2, phosphor-S6 ribosomal protein, CK5, CK8, CK17, vimentin, epithelial cell adhesion molecule (EpCAM), c-Met, cytokeratines, Her2, EGFR, p53, p63, E-cadherin, fragile histidine triad, protein tyrosine phosphatase, β-catenin, p16, c-kit, endothelin-1, endothelin receptor-α, endothelin receptor-β, chemokine (CXC motif) receptor 4, breast cancer resistance protein, ABCA3, MGMT, and any combinations thereof, but it is not limited thereto.

The definition of the term "specifically binding" used herein is the same as the definition of the term typically known to those skilled in the art, and the term refers to an immunological response through specific interaction of an antigen and an antibody. An antibody specifically binding to a surface marker of the target cell may be construed as including a complete antibody as well as antigen binding fragments of the antibody molecule. A naturally occurring complete antibody, or immunoglobulin, includes four polypeptides: two full-length light chains and two full-length heavy chains, in which each light chain is linked to a heavy chain by disulfide bonds. Each heavy chain has a constant region and a variable region. Similarly, each light chain has a constant region and a variable region. There are five heavy chain classes (isotypes): gamma (γ), mu (μ), alpha (α), delta (δ), or epsilon (ε), and additionally several subclasses gamma 1 (γ1), gamma 2(γ2), gamma 3(γ3), gamma 4(γ4), alpha 1(α1), and alpha 2(α2). The light chain constant region can be either kappa (κ) or lambda (λ) type. The term "antigen binding fragment" used herein refers to fragments of an intact immunoglobulin, and any part of a polypeptide including antigen binding regions having the ability to specifically bind to the antigen. For example, the antigen binding fragment may be a F(ab')$_2$ fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment is different from the Fab fragment in that the Fab' fragment additionally includes the hinge region of the heavy chain, including at least one cysteine residue at the C-terminal of the heavy chain CH1 region. The F(ab')$_2$ fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv fragments generally may have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment may be obtained using a protease (for example, a whole antibody is digested with papain to obtain Fab fragments, and is digested with pepsin to obtain F(ab')$_2$ fragments), and may be prepared by a genetic recombinant technique.

The antibody may be a monoclonal antibody, a bispecific antibody, a non-human antibody, a human antibody, a humanized antibody, a chimeric antibody, single chain Fvs (scFV) fragments, a single chain antibody, Fab fragments, F(ab') fragments, disulfide-bond Fvs (sdFV) fragments, an anti-idiotype (anti-Id) antibody, and epitope-binding fragments of these antibodies, but is not limited thereto. In an antibody specifically binding to a surface marker of the target cell, a constant region of the antibody may be bound to a polymer linked to the particle such that an antigen binding site may be exposed.

According to an exemplary embodiment, the particle may further include a protein. According to an exemplary embodiment, the protein may link the polymer to the antibody. The protein may be selected from the group consisting of protein G, protein L, protein A, protein LA, protein AG, and any combinations thereof. The protein is a microorganism-derived protein which binds to a heavy-chain constant region of immunoglobulin. The protein conventionally used for purification of antibodies. By linking the protein to the polymer and antibody, the directionality may be given such that an antigen binding site of the antibody may be directed toward a surface marker of a target cell.

According to an exemplary embodiment, the particle may be selected from the group consisting of polystyrene particle, latex particle, metal particle, glass particle, magnetic particle, and any combinations thereof, but it is not limited thereto. In addition, according to an exemplary embodiment, for example, the particle may have a diameter of about 10 nm to about 10 μm, about 100 nm to about 5 μm, or about 1 μm to about 3 μm. The particle can increase the size of a target cell by binding to the surface marker of the marget cell. For example, because a cancer cell in blood is about 14 μm to about 24 μm in size. A white blood cell ranging from about 10 μm to about 20 μm in size. Thus, it is difficult to selectively isolate the cancer cell from the blood. According to an exemplary embodiment, because the particle links to at least one polymer having negative charges or positive charges, and to which at least one antibody specifically binding to a surface marker of at least one target cell is bound, the particle is positioned around the target cell by binding to the surface marker of the target cell. Thus, the binding of the particle may increase the size of the particle to allow the target cell to be selectively isolated from the blood.

According to another aspect of the present invention, a method for isolating a target cell from a biological sample includes: a) contacting a particle comprising at least one polymer having negative charges and at least one antibody bound to the polymer, wherein the antibody specifically binds to a surface marker of at least one target cell, with a biological sample in a solution; b) adding a particle comprising at least one polymer having positive charges or a particle comprising at least one polymer having positive charges and at least one antibody bound to the polymer, wherein the antibody specifically binds to a surface marker of at least one target cell, into the mixed solution of step a); and c) adjusting a pH value of the mixed solution of step b).

The method for isolating a target cell will be described in detail with each of the following steps:

The method may include: a) contacting a particle comprising at least one polymer having negative charges and at least one antibody bound to the polymer, wherein the antibody specifically binds to a surface marker of at least one target cell, with a biological sample in a solution.

According to an exemplary embodiment, the biological sample may be any biological sample in which the target cell may be present. For example, the sample may be selected from the group consisting of a biopsy sample, a tissue sample, a cell suspension including a separated cell suspended in a liquid medium, a cell culture, and any combinations thereof. In addition, the biological sample may be an animal body fluid. The body fluid may be selected from the group consisting of blood, bone marrow fluid, lymph fluid, saliva, lachrymal fluid, urine, mucous fluid, amniotic fluid, and any combinations thereof, but it is not limited thereto.

For example, in order to isolate a circulating tumor cell, blood may be used as the biological sample.

The contacting may be performed by adding a particle comprising at least one polymer having negative charges and at least one antibody bound to the polymer, wherein the antibody specifically binds to a surface marker of at least one target cell, into a solution including the biological sample. According to an exemplary embodiment, the contacting may be performed in a solution having a pH value equal to or higher than a pKa value of the polymer having negative charges. Then, the particle may be neutral in the solution. The solution serves to provide an environment in which a biological sample and the particle may be stably reacted, and any buffer well known in the art may be used as the solution. The solution may be phosphate buffered saline (PBS) or phosphate buffered saline Tween (PBST), but it is not limited thereto.

According to an exemplary embodiment, the method may further include, before the contacting, pre-treating the biological sample to isolate cells from the biological sample. The cell refers to any cells in the biological sample including the target cell. For example, the pre-treatment may be performed by reducing or removing other materials except for the cells from the sample. The pre-treatment may be selected from the group consisting of centrifugation, filtration, chromatography such as affinity chromatography, and any combinations thereof. For example, when the biological sample is blood, plasma or protein may be removed through the pre-treatment.

In addition, the method may further include, after the contacting, washing the particles unbound to the target cell to remove them.

The washing may be achieved by performing at least one selected from the group consisting of flowing a washing solution, centrifugation, filtration, chromatography, and any combinations thereof to remove or reduce materials other than particles bound to the target cell. The washing solution may be selected from the group consisting of water, buffer (e.g., PBS), physiological saline, and any combinations thereof, but it is not limited thereto.

Subsequently, the method may include: b) adding a particle comprising at least one polymer having positive charges or a particle comprising at least one polymer having positive charges and at least one antibody bound to the polymer, wherein the antibody specifically binds to a surface marker of at least one target cell, into the mixed solution of step a).

In the step a), a particle comprising at least one polymer having negative charges and at least one antibody bound to the polymer, wherein the antibody specifically binds to a surface marker of at least one target cell, is present in a state in which the particle is specifically bound to the target cell in the biological sample. Accordingly, when the particle comprising at least one polymer having positive charges or a particle comprising at least one polymer having positive charges and at least one antibody bound to the polymer, wherein the antibody specifically binds to a surface marker of at least one target cell, is added into the solution of stap a), the particle may be suspended in the mixed solution. In addition, because a pH value of the mixed solution of step a) may be equal to or lower than a pKa value of the polymer having negative charges, a particle comprising at least one polymer having positive charges or a particle comprising at least one polymer having positive charges and at least one antibody bound to the polymer, wherein the antibody specifically binds to a surface marker of at least one target cell, may be positive.

Finally, the method may include: c) adjusting a pH value of the mixed solution of step b).

According to an exemplary embodiment, the adjusting may be performed by adjusting a pH value of the mixed solution of step b) to have a pH value higher than a pKa value of the polymer having negative charges and lower than a pKa value of the polymer having positive charges. For example, when the polymer having negative charges is polymaleic acid and the polymer having positive charges is polyethyleneimine, a pH value in the mixed solution of step b) may be adjusted to higher than about 4 and lower than about 10, specifically about 6 or higher and about 7 or lower.

The pH value may be adjusted by using any acid or base known in the art, which may increase or decrease the pH value. By adjusting the pH value such that it has a value higher than a pKa value of the polymer having negative charges and lower than a pKa value of the polymer having positive charges in the step, a particle comprising at least one polymer having positive charges and at least one antibody bound to the polymer, wherein the antibody specifically binds to a surface marker of at least one target cell, may be negative. Accordingly, an electrostatic attraction forms between the particles having negative charges and the particles having positive charges, and thus aggregation may be occur between particles. Therefore, the overall size of the target cell may be increased, thereby the target cell can be differentiated other cells in a biological sample.

According to an exemplary embodiment, the method further comprises: d) isolating the target cell from the mixed solution of step c). According to an exemplary embodiment, the isolating may be achieved by performing one or more selected from the group consisting of centrifugation, filtration, chromatography, and any combinations thereof. For example, a filter having pores with a size smaaler than that of the increase-sized target cell may be used to isolate the target cell, to allow other cells in a biological sample to pass and prevent the target cell whose overall size has been increased by electrostatic aggregation from passing.

According to an exemplary embodiment, the method may comprise: e-1) adjusting a pH value of the mixed solution of step d) such that the pH value has a value lower than a pKa value of the polymer having negative charges. According to an exemplary embodiment, the method further comprises: f) detecting the target cell.

The step e-1) is a pre-step for detecting the isolated target cell and a process of removing electrostatically aggregated particles unbound to the surface marker of the target cell from the cell whose overall size has been increased. This is step e-1) to adjust the pH value of the mixed solution of step d) in order to remove electrostatic attraction between the particles. That is, by decreasing a pH of the mixed solution of step d), an aggregated particle comprising a polymer having positive charges is dissociated. For example, when the polymer having negative charges is polymaleic acid, and the polymer having positive charges is polyethyleneimine, a pH value of the solution of step e-1) may be adjusted to about 1 or higher and about 5 or lower, or about 2 or higher and about 4 or lower. Subsequently, the target cell in which electrostatically aggregated particle has been removed as above may be detected by electrical or optical methods well known in the art. For example, the target cell may be detected by fluorescent material bound to the particle. In addition, the target cell isolated for detection may be cultured according to cultivation methods well known in the art to be appropriately used for experimental purposes.

According to another aspect of the present invention, a method for isolating a target cell from a biological sample, the method comprising: a) contacting a particle comprising at least one polymer having positive charges and at least one antibody bound to the polymer, wherein the antibody specifically binds to a surface marker of at least one target cell, with the biological sample in a solution; b) adding a particle comprising at least one polymer having negative charges or a particle comprising at least one polymer having negative charges and at least one antibody bound to the polymer, wherein the antibody specifically binds to a surface marker of at least one target cell, into the mixed solution of step a); and c) adjusting a pH value of the mixed solution of step b).

Because the method for isolating a target cell described above, each step will be described by omitting what are common between the two methods in order to avoid the excessive complexity of the specification:

The method may include: a) contacting a particle comprising at least one polymer having positive charges and at least one antibody bound to the polymer, wherein the antibody specifically binds to a surface marker of at least one target cell, with the biological sample in a solution.

According to an exemplary embodiment, the contacting may be performed in a solution having a pH value equal to or smaller than a pKa value of the polymer having positive charges. Then, the particle may be neutral in the solution.

According to an exemplary embodiment, the method may further include, before the contacting, pre-treating the biological sample to isolate cells from the biological sample. In addition, the method may further include, after the contacting, washing the particles unbound to the target cell.

Subsequently, the method include: b) adding a particle comprising at least one polymer having negative charges or a particle comprising at least one polymer having negative charges and at least one antibody bound to the polymer, wherein the antibody specifically binds to a surface marker of at least one target cell, into the mixed solution of step a).

In the step a), a particle comprising at least one polymer having positive charges and at least one antibody bound to the polymer, wherein the antibody specifically binds to a surface marker of at least one target cell is specifically bound to the target cell in the biological sample. When the particle comprising at least one polymer having negative charges or a particle comprising at least one polymer having negative charges and at least one antibody bound to the polymer, wherein the antibody specifically binds to a surface marker of at least one target cell, is added into the mixed solution of step a), the particle may be suspended in the mixed solution. In addition, because a pH value of the mixed solution of step a) may be equal to or higher than a pKa value of the polymer having positive charges, a particle comprising a polymer having negative charges or a particle comprising a polymer having negative charges and at least one antibody bound to the polymer, wherein the antibody specifically binds to a surface marker of at least one target cell, may be negative.

Finally, the method may include: c) adjusting a pH value of the mixed solution of step b).

According to an exemplary embodiment, the pH value of the mixed solution of step b) is adjusted to a value higher than a pKa value of the polymer having negative charges and lower than a pKa value of the polymer having positive charges. For example, when the polymer having positive charges is polyethyleneimine and the polymer having negative charges is polymaleic acid, a pH value in the mixed solution of step b) may be adjusted to higher than about 4 and lower than about 10, specifically about 6 or higher and about 7 or lower.

The pH value may be adjusted by using any acid or base known in the art, which may increase or decrease the pH value. By adjusting the pH value such that it has a value higher than a pKa value of the polymer having negative charges and lower than a pKa value of the polymer having positive charges in the step, a particle comprising at least one polymer having positive charges and at least one antibody bound to the polymer, wherein the antibody specifically binds to a surface marker of at least one target cell, may be positive, while a particle comprising the polymer having negative charges, the particle including an antibody specifically binding to an surface marker of at least one target cell bound to the polymer, may be negative. Accordingly, an electrostatic attraction forms between the particles having negative charges and the particles having positive charges, and thus aggregation may occur between particles. Therefore, the overall size of the target cell may be increased, thereby the target cell can be differentiated other cells in a biological sample.

According to an exemplary embodiment, the method may further comprise: d) isolating the target cell from the mixed solution of step c). According to an exemplary embodiment, the isolating may be achieved by performing one or more selected from the group consisting of centrifugation, filtration, chromatography, and any combinations thereof.

According to an exemplary embodiment, the method may comprise: e-2) adjusting a pH value of the mixed solution of step d) such that the pH value has a value higher than a pKa value of the polymer having positive charges. According to an exemplary embodiment, the method further comprises: f) detecting the target cell. The step e-2) is a pre-step for detecting the isolated target cell and a process of removing electrostatically aggregated particles unbound to the surface marker of the target cell from the cell whose overall size has been increased. This is step e-2) to adjust the pH value of the mixed solution of step d) in order to remove electrostatic attraction between the particles. That is, by increasing a pH of the mixed solution of step d), an aggregated particle comprising a polymer having negative charges is dissociated. For example, when the polymer having positive charges is polyethyleneimine and the polymer having negative charges is polymaleic acid, a pH value of the solution of step e-2) may be adjusted to about 9 or higher and about 14 or lower, specifically about 10 or higher and about 12 or lower. Subsequently, the target cell in which electrostatically aggregated particle has been removed as above may be detected by electrical or optical methods well known in the art. In addition, the target cell isolated for detection may be cultured according to cultivation methods well known in the art to be appropriately used for experimental purposes.

According to another aspect of the present invention, a kit for isolating a target cell from a biological sample, the kit comprising: a) a particle comprising at least one polymer having negative charges and at least one antibody bound to the polymer, wherein the antibody specifically binds to a surface marker of at least one target cell and a particle comprising at least one polymer having positive charges and at least one antibody bound to the polymer, wherein the antibody specifically binds to a surface marker of at least one target cell; b) the particle comprising at least one polymer having negative charges and at least one antibody bound to the polymer, wherein the antibody specifically binds to a surface marker of at least one target cell and a particle comprising at least one polymer having positive charges; or c) the particle particle comprising at least one polymer having positive charges and at least one antibody bound to the polymer, wherein the antibody specifically binds to a surface marker of at least one target cell and a particle comprising at least one polymer having negative charges.

According to an exemplary embodiment, the kit may further comprise a filter having pores.

The kit may be manufactured by varying the antibody according to the type of a target cell to be isolated and by varying a pore diameter according to the size of a target cell. According to an exemplary embodiment, the kit may be manufactured to have a pore diameter of, for example, about 1 μm to about 100 μm, about 3 μm to about 50 μm, or about 8 μm to about 30 μm.

One or more embodiments of the present invention will be described in further detail with reference to the following examples. These examples are for illustrative purposes only and are not intended to limit the scope of the one or more embodiments of the present invention.

BRIEF DESCRIPTION OF DRAWINGS

These and/or other aspects will become apparent and more readily appreciated from the following description of the embodiments, taken in conjunction with the accompanying drawings of which.

MODE FOR THE INVENTION

Figure 1:
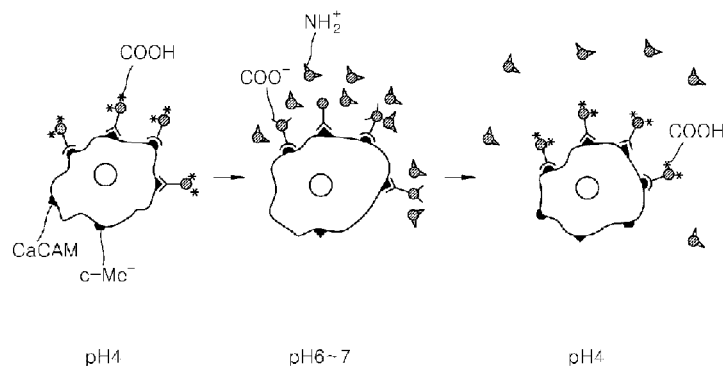
FIGS. 1 and 2 are views schematically illustrating a method for isolating a target cell according to an exemplary embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Figure 2:
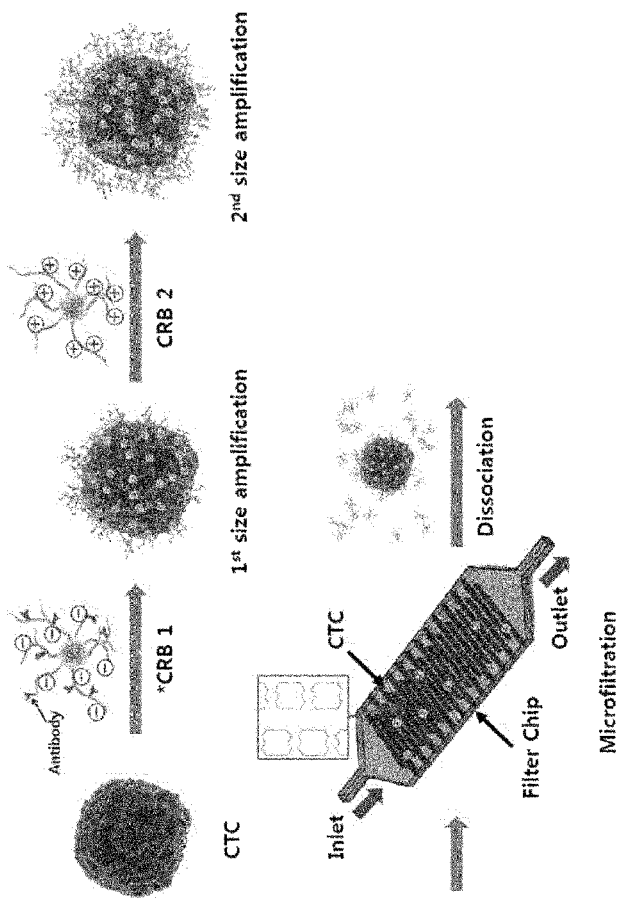

FIGS. 1 and 2 are schematic views of a method for isolating a target cell according to an exemplary embodiment, and show a method for isolating circulating tumor cells from blood.

Hemocyte cells such as white blood cell and red blood cell are present together in a blood sample including circulating tumor cells, and the size of the circulating tumor cells is similar to that of white blood cell in the blood sample and thus the circulating tumor cells may not be isolated by size. Accordingly, the overall size of the circulating tumor cells may be increased by the method and thus the circulating tumor cells may be isolated from other hemocyte cells by filtration.

In order to increase the overall size of the circulating tumor cells, the method utilizes a principle of aggregating particles on the surface of the cell. In order to aggregate particles on the cell surface, a polymer, whose electrostatic properties may be changed according to the pH value of the ambient environment, is linked to the particles, and a marker (for example, EpCAM and/or C-Met) shown on the surface of the circulating tumor cells is used for the particles bound to the polymer in order to specifically aggregate the circulating cancer cells only.

Referring to FIG. 1 to describe the method, a blood including circulating tumor cells is first obtained, the sample is suspended in a buffer with a pH of about 3 to about 4, and a particle, whose surface has an acrylic acid-maleic acid copolymer or a styrene sulfonic acid-maleic acid copolymer and to which at least one antibody of EpCAM and/or C-Met is bound, is added into the buffer to contact the circulating tumor cells with the particle. At the time, the antibody of EpCAM and/or C-Met bound to the particle binds specifically to EpCAM and/or C-Met in circulating tumor cells and thus the particle to which the antibody is bound is positioned around the circulating tumor cell through the antibody. In addition, the acrylic acid-maleic acid copolymer or the styrene sulfonic acid-maleic acid copolymer, linked to the particle, has a pKa value of about 4, and thus the particle is neutral in the buffer.

Subsequently, when a particle having polyethyleneimine is added into the buffer and a pH of the buffer is increased to about 6 to about 7, an imine group on the particle having polyethyleneimine shows positive charges while a carboxylic group or a sulfonic group on the particle having the acrylic acid-maleic acid copolymer or the styrene sulfonic acid-maleic acid copolymer shows negative charges. As shown in FIG. 1, a particle having polyethyleneimine, the particle dissociated around a particle specifically bound to EpCAM and/or C-Met in the existing circulating tumor cells, may be aggregated by electrostatic attraction. The overall size of the circulating tumor cells is increased by the aggregated particles, and as a result, the cells have sizes much bigger than those of other hemocyte cells in a blood sample. The circulating tumor cells with their sizes increased by this method may be isolated through filtration. When a pH of the buffer is reduced to about 4 as in the initial step prior to the isolating or the pH reduction is performed according to the purpose so as to remove the aggregated particles after the isolating, the particle having the polyethyleneimine becomes neutral as shown in FIG. 1. As a result, the particle may be dissociated. The Examples show experimental results according to the principle.

Example 1

Manufacture of a Particle Having Charges (Charge Reversible Bead, CRB)

A particle having negative charges in a neutral pH and a particle having positive charges in a neutral pH were each manufactured in the following manner.

First, polystyrene beads (Polysciences, Inc) with a diameter of about 1 µm to about 3 µm were prepared, and then a particle having negative charges in a neutral pH was manufactured by treating the polystyrene beads with N-hydroxysuccinimide (NHS)/1-ethyl-3-[3-dimethylaminopropyl] carbodiimide hydrochloride (EDC) and linking an acrylic acid-maleic acid copolymer or a styrene sulfonic acid-maleic acid copolymer to the polystyrene beads. A polystyrene particle having the acrylic acid-maleic acid copolymer was referred to as CRB 1-1, and a polystyrene particle having the styrene sulfornic acid-maleic acid copolymer was referred to as CRB1-2. In addition, a particle having positive charges in a neutral pH was manufactured by treating the polystyrene beads with NHS/EDC and linking a linear polyethyleneimine polymer, a branched polyethyleneimine polymer, or chitosan to the polystyrene beads. A polystyrene particle having the linear polyethyleneimine polymer was referred to as CRB2-1, a polystyrene particle having the branched polyethylene polymer was referred to as CRB2-2, and a polystyrene particle having chitosan was referred to as CRB2-3. The CRB2-1, CRB2-2, and CRB2-3 were manufactured by linking Texas Red for giving a red fluorescence to them.

Example 2

Figure 3:
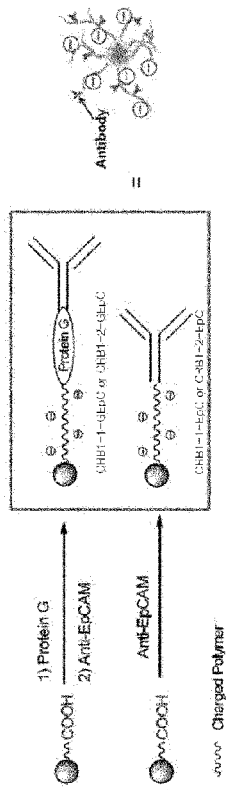
FIG. 3 is a schematic view of a particle having negative charges, the particle having an antibody, according to an exemplary embodiment.

Manufacture of a Particle having Negative Charges, the Particle to Which an Antibody is Bound As a cell used as a target cell to be isolated according to the principle was a breast cancer cell line MCF-7 (Korea Cell Line Bank), an antibody (Human EpCAM/TROP1 Fluorescein MAb (Clone 158206), FAB9601F, R&S system) specifically binding to EpCAM as a surface marker of a cancer cell existing therein was selected. Subsequently, the CRB1-1 or CRB1-2 manufactured in Example 1 was put into a PBS solution including 5% BSA, an antibody (0.65 mg/ml) specifically binding to EpCAM is added into the resulting solution, and the mixture was gently stirred at room temperature for about 2 hours. As a result, CRB1-1 (referred to as CRB1-1-EpC) or CRB1-2 (referred to as CRB1-2-EpC) having an antibody specifically binding to EpCAM was manufactured. In addition, in order to enhance the directionality during binding of the antibody, CRB1-1 or CRB1-2 was put into a PBS solution including 5% BSA, protein G (0.65 mg/ml) was added to the resulting solution for reaction for about 2 hours, and then an antibody (0.65 mg/ml) specifically binding to EpCAM was added into the reaction mixture while being gently stirred for about 2 hours. As a result, an antibody specifically binding to EpCAM and CRB 1-1 (referred to as CRB1-1-GEpC) or CRB1-2 (referred to as CRB1-2-GEpC), to which protein G is bound, was manufactured. FIG. 3 shows a schematic view of the particle having an antibody.

Example 3

Identification of Aggregation and Dissociation Between CRBs

Figure 4:
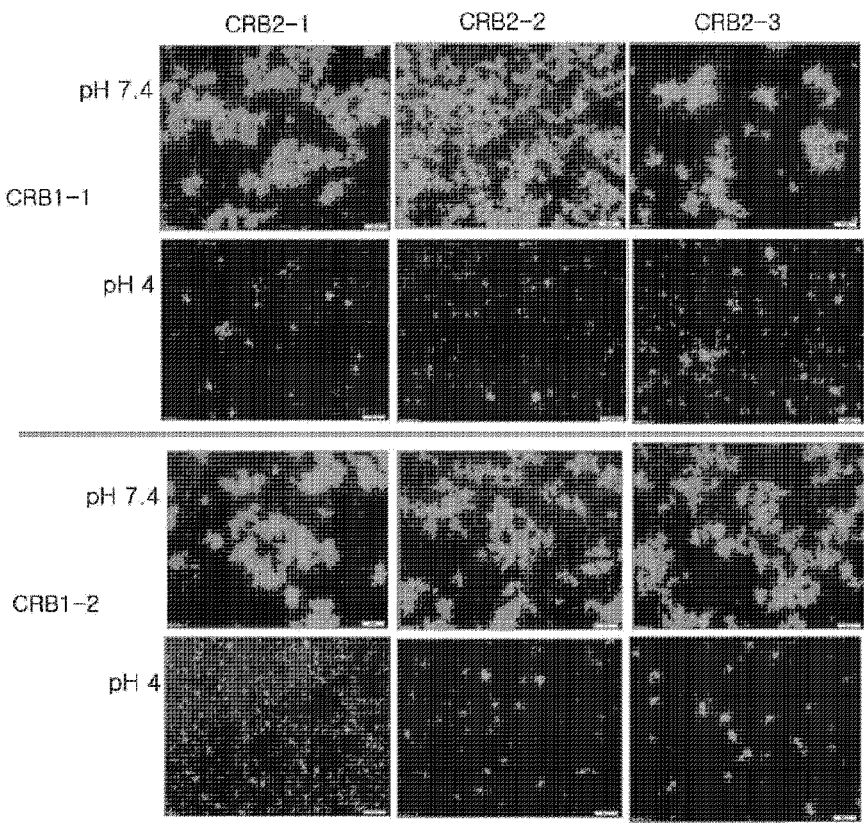
FIG. 4 is a set of fluorescent microscopic photos illustrating results of aggregation and dissociation between CRBs (CRB1-1 or CRB1-2 and CRB2-1, CRB2-2 or CRB2-3) according to an exemplary embodiment.

When the CRBs manufacture in Examples 1 and 2 were mixed, experiments were performed to see whether the CRBs may be aggregated and dissociated according to the pH of the ambient environment. Each of 30 µl of CRB2-1, CRB2-1, and CRB2-3 was mixed with each of 30 µl of CRB1-1 in a test tube including a PBS solution, a NaOH solution was added portionwise into the resulting solution, the pH was titrated to about 7.4, and the mixture was allowed to stand for about 1 hour. For CRB 1-2, the aggregation and dissociation was performed in the same manner as above. In the process, NaOH was added for reaction for about 1 hour, HCl was added for reaction for about 1 hour, and then a fluorescent microscope (Olympus IX-81) was used to identify whether the particles had been aggregated and dissociated. It was identified by an observation of the intensity of fluorescence of Texas Red through the fluorescent microscope that the two different kinds of particles had been aggregated and that the two different kinds of particles had been dissociated when the pH of the ambient environment was decreased to about 4 (FIG. 4).

Example 4

Identification of Binding Between CRB1 and Cancer Cell

Figure 5:
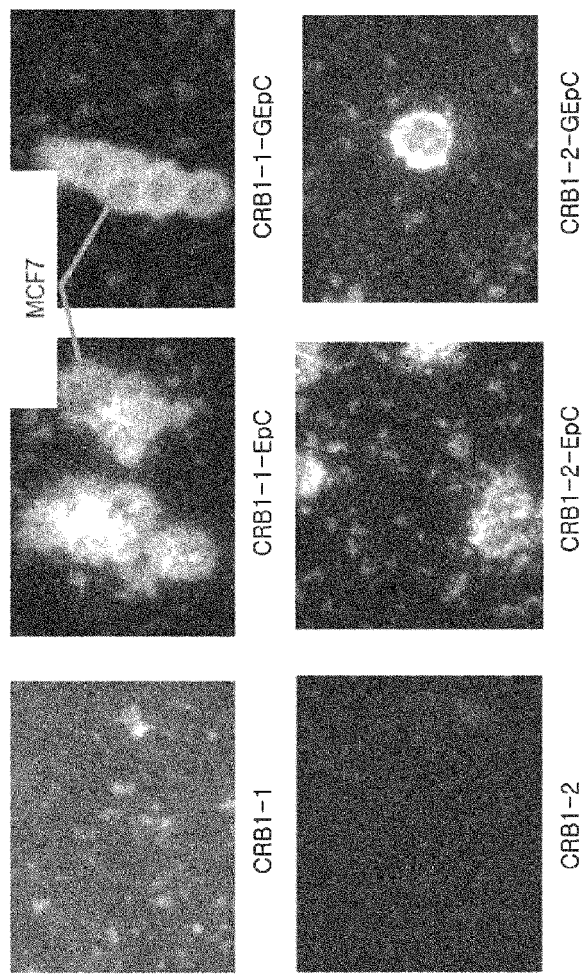
FIG. 5 is a set of fluorescent microscopic photos illustrating results of binding between CRB1s(CRB1-1, CRB1-1-EpC, CRB1-1-GEpC, CRB1-2, CRB1-2-EpC or CRB1-2-GEpC) and MCF-7 cells, according to an exemplary embodiment.
Figure 6:
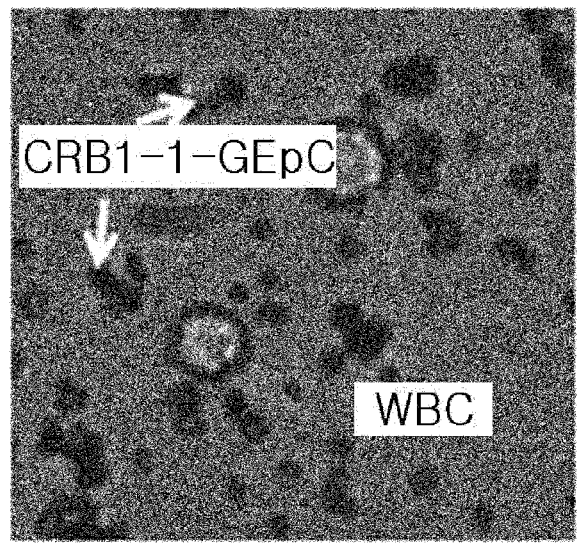
FIG. 6 is a fluorescent microscopic photo illustrating a result of binding between CRB1-1-GEpC and white blood cells according to an exemplary embodiment.

Each of 30 µl of the CRB1-EpC, CRB1-2-EpC, CRB1-1-GEpC, or CRB1-2-GEpC manufactured in Example 2 was added into breast cancer cell MCF-7 ($1 \times 10^5$ cells) in DMEM medium and allowed to stand for about 1 hour. It was identified by the fluorescence intensity of fluorescein using a fluorescent microscope (Olympus IX-81) whether MCF-7 had been bound to CRB1-1-EpC, CRB1-2-EpC, CRB1-1-GEpC, or CRB1-2-GEpC (FIG. 5). As a result, it was confirmed that the added particles had bound to cancer cell to increase the overall size of the cancer cell than the original size of the cancer cell. On the contrary, the same experiment as in the Example was performed as a control experiment to see whether white blood cell isolated from a blood sample had been bound to CRB-1, and it was identified that the binding as above had not occurred in white blood cell (FIG. 6).

Example 5

Identification of Aggregation and Dissociation between Cancer Cell to which CRB1 is Bound and CRB2

Figure 7:
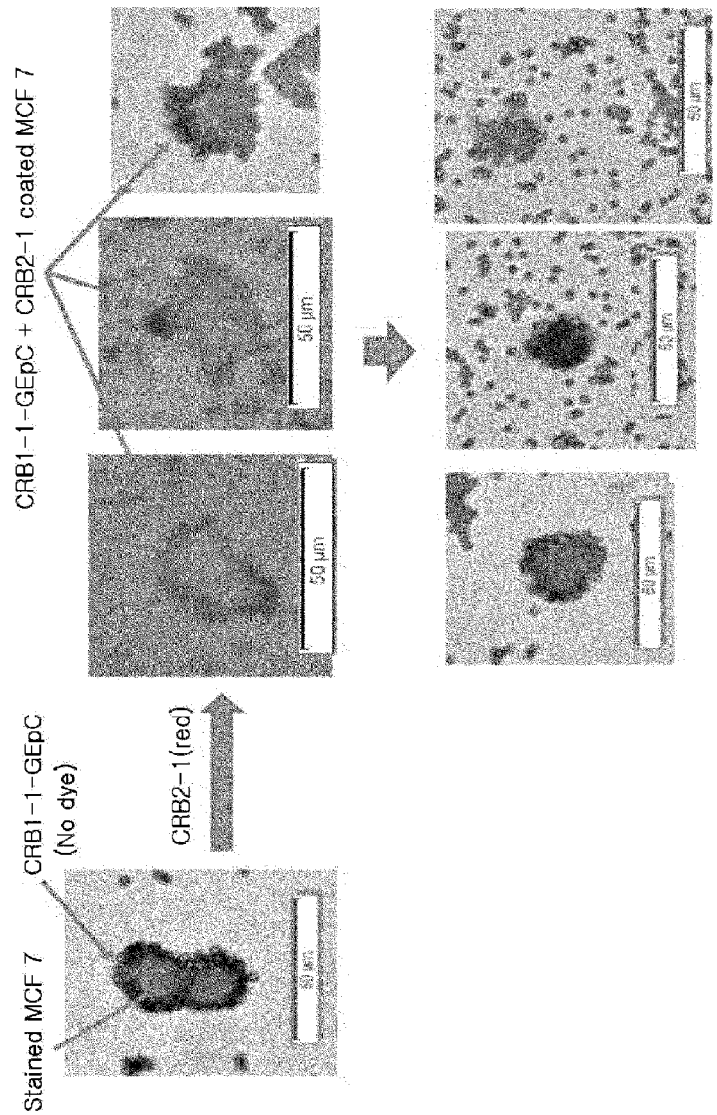
FIG. 7 is a set of fluorescent microscopic photos illustrating results of binding between CRB1-1-GEpC and MCF-7 cells and aggregation and dissociation between CRB1-1-GEpC, which are bound to MCF-7 cells, and CRB2-1 according to an exemplary embodiment.

30 µl of the CRB1-1-GEpC manufactured in Example 2 and breast cancer cell MCF-7 ($1\times10^5$ cells) stained with Hoechst33342 were mixed in a test tube including a PBS solution, the resulting solution was allowed to stand for about 1 hour, and then it was identified by a fluorescent microscope (OlympusIX-81) whether MCF-7 had been bound to CRB1-1-GEpC. As a result, it was confirmed that CRB1-1-GEpC had been bound to MCF-7 (FIG. 7). Subsequently, 30 µl of the CRB2-1 manufactured in Example 1 was added into MCF-7 to which CRB1-1-GEpC was bound, a NaOH solution was added portionwise into the resulting solution, the pH was titrated to about 7.4, the mixture was allowed to stand for about 1 hour, and then an observation was made by using a fluorescent microscope (Olympus IX-81) (FIG. 7). As a result, it was identified that the added CRB2-1 was aggregated in MCF-7 to which CRB1-1-GEpC was bound to increase the overall size than the original size of MCF-7. Subsequently, a HCl solution was added portionwise into the solution, the pH was titrated to about 3, and the mixture was allowed to stand for about 1 hour. As a result, when the pH of the solution was lowered to about 3, it was identified that the aggregated CRB2-2 had been dissociated from the MCF-7 to which CRB1-1-GEpC had been bound (FIG. 7).

Figure 8:
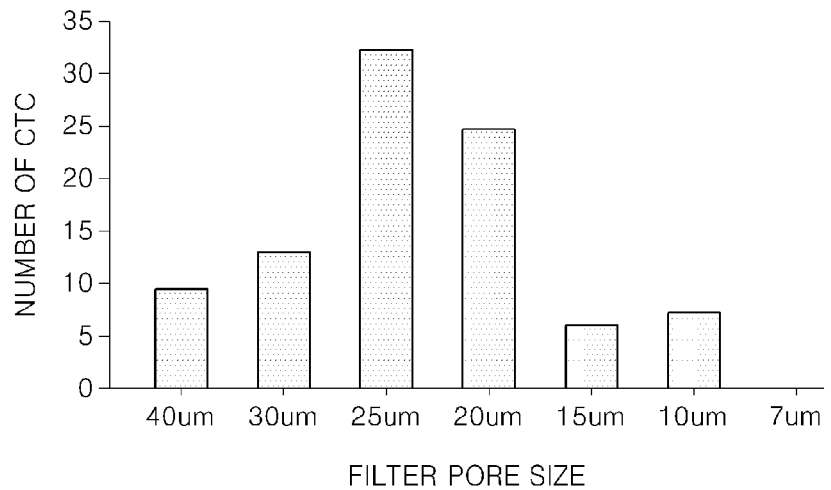
FIG. 8 is a graph illustrating results of separating MCF-7 to which CRB1-1-GEpC is bound by using a fine filter, according to an exemplary embodiment.

The CRB2-1 had been dissociated, and then only the MCF-7 to which CRB1-1-GEpC had been bound was isolated by using a fine filter with a pore size of about 7 µm to about 40 µm. A solution including MCF-7 to which CRB1-1 had been bound was flowed into the fine filter at a rate of about 10 ul/min, and an operation was performed such that about 100 cells per ml might be included in the solution. As shown in FIG. 8, an experiment was performed 5 times, and it was confirmed that the average recovery ratio of MCF-7 to which CRB1-1-GEpC had been bound was about 91% and the isolation of MCF-7 to which CRB1-1-GEpC had been bound was excellent when a fine filter with a pore size of about 20 µm to about 25 µm was used. On the contrary, the isolated cell was inoculated into a cell culture plate including a DMEM medium and the content was cultured under conditions of 37° C. and 5% $CO_2$ for about 24 hours. As a result, it was identified that the cell had been grown in the same way as in the MCF-7 cell as a control group.

Example 6

Test of Binding Between Cancer Cell Included in Blood Without a Pretreatment and CRB1

Figure 9:
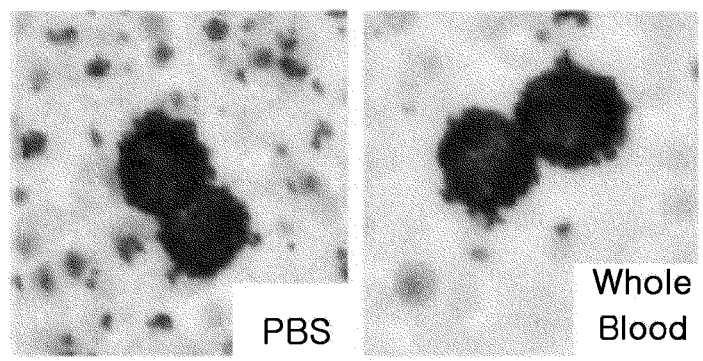
FIG. 9 and FIG. 10 are fluorescent microscopic photos and a graph illustrating a result of binding between CRB1-1-GEpC and MCF-7 cell included in whole blood which is not pre-treated, according to an exemplary embodiment.
Figure 10:
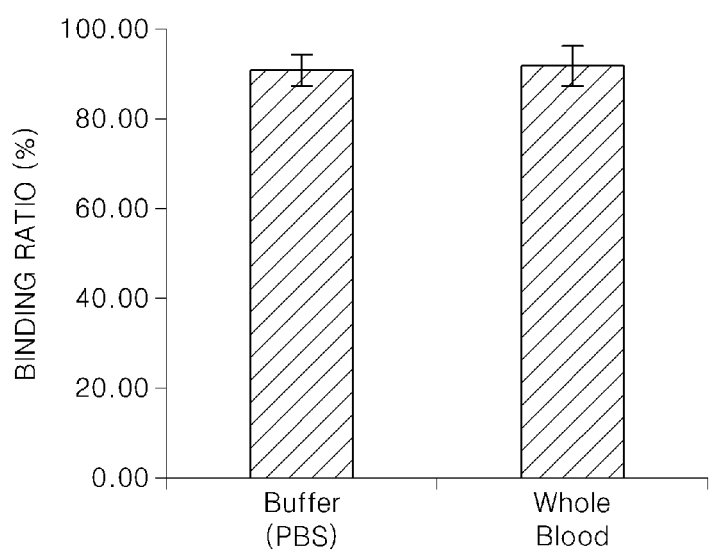

30 µl of the CRB1-1-GEpC manufactured in Example 2 was added into 1 ml of blood including 50 cells of MCF-7, the resulting solution was allowed to stand for about 1 hour, and it was observed by a fluorescent microscope (Olympus IX-81) in Bright Field mode whether CRB1-1-GEpC had been bound to MCF-7 (FIG. 9). In order to calculate a binding ratio of CRB1-1-GEpC to MCF-7, the amount of the CRB1-1-GEpC bound to the cell was converted into an area. A PBS solution including 50 cells of MCF-7 was used as a comparison group. As shown in FIG. 9 and FIG. 10, even when a blood sample including MCF-7 was not subjected to a pretreatment, it was identified that CRB1-1-GEpC has been bound to MCF-7 cell.

Example 7

Figure 11:
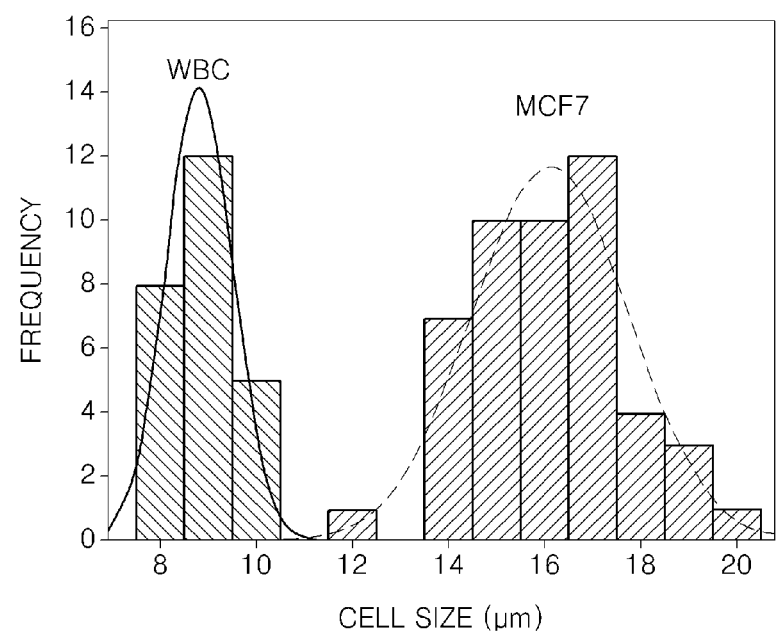
FIG. 11, FIG. 12 and FIG. 13 are graphs of normal distribution illustrating sizes of MCF-7 cells according to aggregation reactions between CRB1-1-GEpC, which are bound to MCF-7 cell and CRB2-1.
Figure 12:
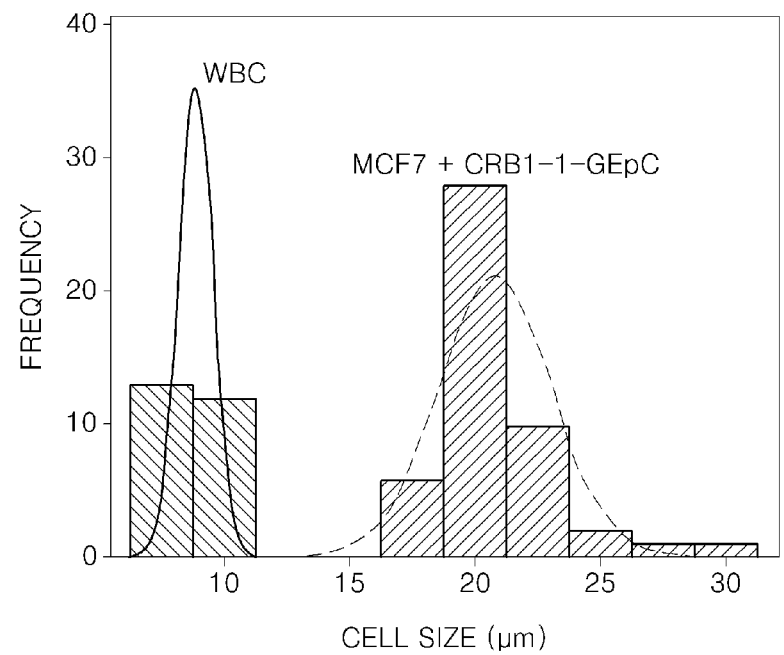
Figure 13:
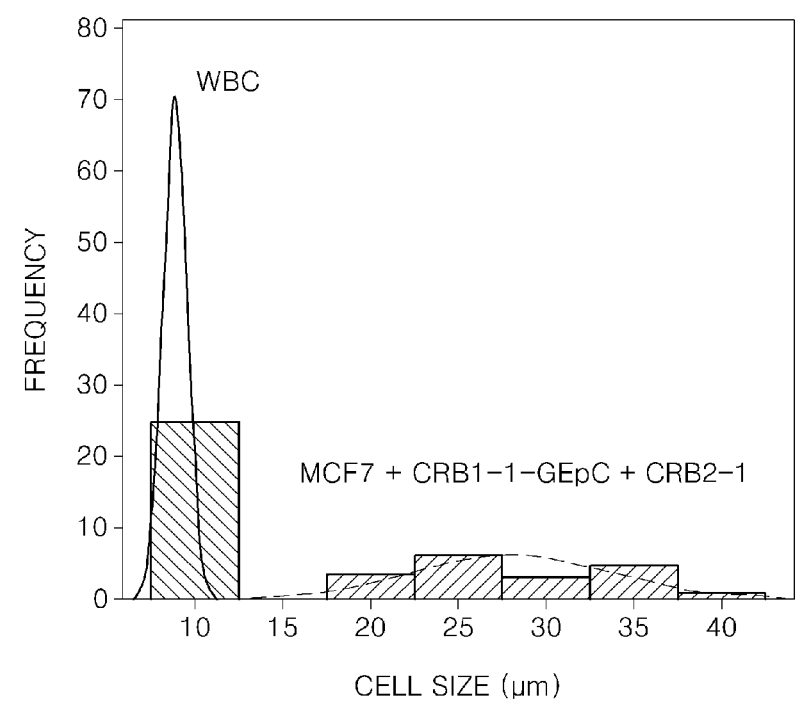
Figure 14:
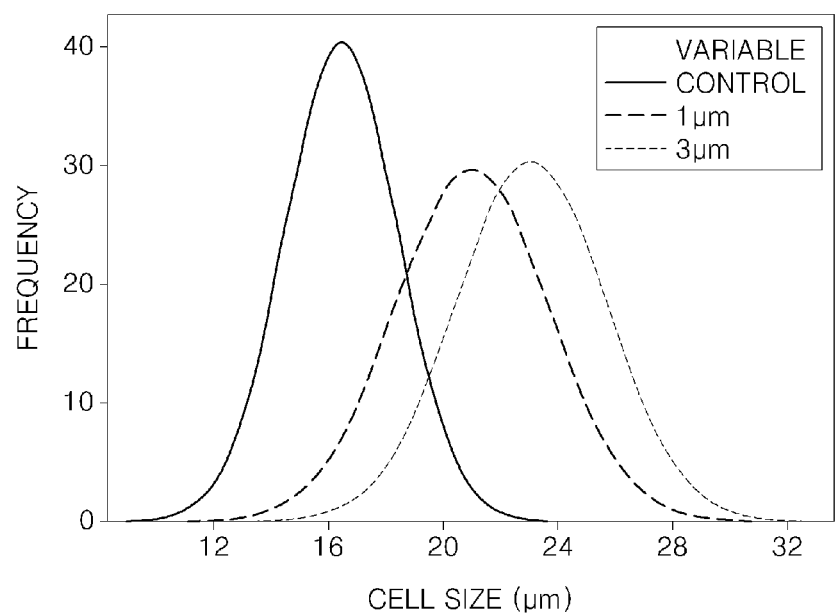
FIG. 14 is a graph of normal distribution illustrating sizes of MCF-7 cells to which CRB1-1-GEpC is bound according to the size of particles used.

Size Comparison Test Between a Cancer Cell to which CRB1 is Bound, Aggregated by CRB2, and a Cancer Cell to which CRB1 is Bound According to the Size of Particle The CRB1-1-GEpC manufactured in Example 2 was used to allow the CRB1-1-GEpC to bind to MCF-7 cell in the same manner as in Example 5, and then the sizes of MCF-7 cells to which CRB1-1-GEpC had been bound were observed by a fluorescent microscope (Olympus IX-81) in Bright Field mode (n=100). White blood cell was used as a comparison experiment instead of MCF-7 cell while MCF-7 to which CRB1-1-GEpC had not been bound was used as a control group (FIG. 11). As shown in FIG. 12, the size of MCF-7 to which CRB1-1-GEpC had been bound was about 20 µm, and it was identified that the size had been increased by about 4 µm to about 10 µm, as compared to the size of MCF7 to which CRB 1-1-GEpC had not been bound. In addition, CRB1-1-GEpC was bound to the MCF-7 cell, and then an aggregation reaction was performed by adding CRB2-1 into the mixture. As shown in FIG. 13, it was identified that the size had been increased by about 8 µm to about 20 µm, as compared to the size of MCF-7 to which CRB1-1-GEpC had not been bound. The size of monocyte in white blood cell was known to be about 14 µm to about 20 µm. Accordingly, when CRB1-1-GEpC bound to MCF-7 cell and CRB2-1 was aggregated to the mixture, the difference in sizes of other white blood cells may be increased to isolate the MCF-7 cell in blood. In addition, even when CRB2-1 was not aggregated, the difference in sizes of other white blood cells may be generated by increasing the size of polystyrene bead in the CRB1-1-GEpC. As shown in FIG. 14, when the size of polystyrene bead with which CRB1-1-GEpC was made was increased from about 1 µm to about 3 µm, it was identified that the size of MCF-7 cell to which CRB1-1-GEpC was bound had been increased by about 2 µm.

Example 8

A Target Cell Isolation Method Using a Kit for Isolating a Target Cell

Figure 15:
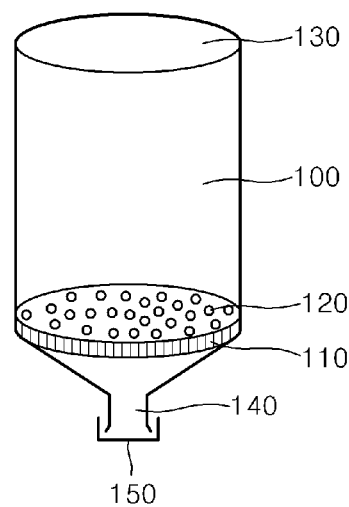
FIG. 15 is a schematic view of a kit for isolating a target cell according to an exemplary embodiment.

FIG. 15 is a schematic view of a kit for isolating a target cell according to an exemplary embodiment. Referring to FIG. 12, an isolation and detection process of the circulating tumor cells will be described with reference to examples.

First, a blood sample is suspended in a buffer with a pH of about 3 to about 4, and the suspension is injected into an upper opening 130 of a filter column 100. In order to prevent a sample from spilling, a lower opening 140 of the filter column 100 may be sealed with a cap 150. Because CRB1-1-EpC, CRB1-2-EpC, CRB1-1-GEpC, or CRB1-2-GEpC is included in the filter column 100, the particle may be contacted with circulating tumor cell in the blood sample. Subsequently, CRB2-1, CRB2-2, or CRB2-3 is added into the upper opening 130 of the filter column, followed by pH adjustment with a buffer included in the filter column 100 to about 6 to about 7. At the time, the pH may be adjusted by adding an acid solution into the filter column 100. Subsequently, as described above, an aggregation reaction occurs in the filter column 100, and the sizes of circulating tumor cells have been increased by the aggregated particles to prevent the cells from passing through pores 120 in a filter 110. Accordingly, the cells remains in the filter column 100 while other hemocyte cells and polymers pass through the filter 110 to be drained into the lower opening 140 of the filter column 100. Subsequently, in order to detect the circulating tumor cells, a base solution may be added into the filter column 100 and CRB2-1, CRB2-2, or CRB2-3 may be isolated and removed from the filter column 100. A circulating tumor cell from which the CRB2-1, CRB2-2, or CRB2-3 has been removed may be isolated in a state in which CRB1-1-EpC, CRB1-2-EpC, CRB1-1-GEpC, or CRB1-2-GEpC is bound to the cell. The isolated cell may be cultured in the same way as in methods known in the art. After the culture, trypsin may be treated to separately isolate only circulating tumor cells.

A target cell in a biological sample may be efficiently isolated and detected by using a method and kit for isolating the target cell from the biological sample according to an exemplary embodiment.

It should be understood that the exemplary embodiments described therein should be considered in a descriptive sense only and not for purposes of limitation. Descriptions of features or aspects within each embodiment should typically be considered as available for other similar features or aspects in other embodiments.

The invention claimed is:

1. A method for isolating a target cell from a biological sample, the method comprising:
   a) contacting a particle comprising at least one polymer having negative charges and at least one antibody bound to the polymer with a biological sample in a solution to provide a mixed solution, wherein the antibody specifically binds to a surface marker of at least one target cell;
   b) adding a particle comprising at least one polymer having positive charges, or a particle comprising at least one polymer having positive charges and at least one antibody bound to the polymer, into the mixed solution of step a);
   c) adjusting a pH value of the mixed solution of step b); and
   d) isolating the target cell from the mixed solution of step c); or
   a) contacting a particle comprising at least one polymer having positive charges and at least one antibody bound to the polymer with a biological sample in a solution to provide a mixed solution, wherein the antibody specifically binds to a surface marker of at least one target cell;
   b) adding a particle comprising at least one polymer having negative charges, or a particle comprising at least one polymer having negative charges and at least one antibody bound to the polymer, into the mixed solution of step a);
   c) adjusting a pH value of the mixed solution of step b); and
   d) isolating the target cell from the mixed solution of step c).

2. The method of claim 1, wherein the pH value of the solution is adjusted to a value higher than a pKa value of the polymer having negative charges and lower than a pKa value of the polymer having positive charges.

3. The method of claim 1, wherein isolating the target cell from the mixed solution of step c is achieved by centrifugation, filtration, chromatography, or a combination thereof.

4. The method of claim 1, wherein the biological sample is an animal body fluid, or cells isolated from an animal body fluid, optionally wherein the body fluid is blood, bone marrow fluid, lymph fluid, saliva, lachrymal fluid, urine, mucous fluid, amniotic fluid, or combination thereof.

5. The method of claim 1, wherein the method further comprises, after step b):
   b-1) adjusting a pH value of the mixed solution to a value lower than a pKa value of the polymer having negative charges; or
   b-2) adjusting a pH value of a mixed solution of step d) to a value higher than a pKa value of the polymer having positive charges.

6. The method of claim 5, wherein the method further comprises detecting the target cell.

7. The method of claim 1, wherein the charges are negative and the polymer is polystyrenesulfonate, polyacrylic acid, polymethacrylic acid, polyalcohol, polyphosphate, polymaleic acid, hyaluronic acid, or combination thereof.

8. The method of claim 1, wherein the charges are positive and the polymer is polyaniline, polypyrrol, polyethyleneimine, polylysine, chitosan, or combination thereof.

9. The method of claim 1, wherein the particle further comprises a protein which links the polymer to the antibody.

10. The method of claim 9, wherein the protein is protein G, protein L, protein A, protein LA, protein AG, or combination thereof.

11. The method of claim 1, wherein the polymer is a linear polymer or a branched polymer.

12. The method of claim 1, wherein the particle is a polystyrene particle, latex particle, metal particle, glass particle, magnetic particle, or combination thereof.

13. The method of claim 1, wherein the target cell has a surface marker on a cell surface.

14. The method of claim 1, wherein the target cell is a circulating tumor cell, cancer stem cell, immunocyte, fetal stem cell, fetal cell, cancer cell, or tumor cell.

15. The method of claim 1, wherein the surface marker is protein, polysaccharide, lipid, nucleic acid, or combination thereof.

16. The method of claim 1, wherein the surface marker is an estrogen receptor, progesterone receptor, synaptophysin, mucin 1 (MUC 1), Bcl-2, MIB1/Ki67, cyclin D1, cyclin E, p27, topoisomerase IIa, cyclooxygenase 2, ERK1/ERK2, phosphor-S6 ribosomal protein, CK5, CK8, CK17, vimentin, epithelial cell adhesion molecule (EpCAM), c-Met, cytokeratins, Her2, EGFR, p53, p63, E-cadherin, fragile histidine triad, protein tyrosine phosphatase, $\beta$-catenin, p16, c-kit, endothelin-1, endothelin receptor-$\alpha$, endothelin receptor-$\beta$, chemokine (CXC motif) receptor 4, breast cancer resistance protein, ABCA3, MGMT, or combination thereof.

* * * * *